United States Patent [19]

Faruk et al.

[11] Patent Number: 4,902,801
[45] Date of Patent: Feb. 20, 1990

[54] PROCESS FOR PREPARING ARYL-PIPERIDINE CARBINOLS AND NOVEL INTERMEDIATES USED IN THE PROCESS

[75] Inventors: Erol A. Faruk; Roger T. Martin, both of Harlow, England

[73] Assignee: Beecham Group plc., Brentford, England

[21] Appl. No.: 894,695

[22] Filed: Aug. 8, 1986

[30] Foreign Application Priority Data

Aug. 10, 1985 [GB] United Kingdom ............... 8520153
May 23, 1986 [GB] United Kingdom ............... 8612579

[51] Int. Cl.⁴ ............... C07D 211/22; C07D 211/32; C07D 211/40
[52] U.S. Cl. ............................... 546/220; 546/240
[58] Field of Search ........................... 546/240, 220

[56] References Cited

U.S. PATENT DOCUMENTS

| | | | |
|---|---|---|---|
| 3,161,647 | 12/1964 | Denss et al. | 546/220 |
| 3,440,245 | 4/1969 | Kato et al. | 546/220 |
| 3,666,746 | 5/1972 | Stanley et al. | 546/219 X |
| 3,681,327 | 8/1972 | Newman | 546/219 X |
| 3,947,460 | 3/1976 | Houlihan | 546/219 X |
| 4,007,196 | 2/1977 | Christensen et al. | 260/293.58 |
| 4,585,777 | 4/1986 | Lassen et al. | 514/317 |

FOREIGN PATENT DOCUMENTS 0047516 3/1982 European Pat. Off. .
1422263 1/1976 United Kingdom .

OTHER PUBLICATIONS

Vorlander; Annalen der Chemie, 320 (1902), pp. 66–92.
Brown et al.; J. Org. Chem. 84 (1969), pp. 3920–3921.
Clarke et al.; J. Med. Chem., (1973), 16, pp. 1260–1267.
House; "Modern Synthetic Reactions" (2nd Ed.) 1972, page 72.

Shigeo et al.: C.A. 91(1979), 91:211258g.
J. March in *Advanced Organic Chemistry* by McGraw-Hill (1977), 2nd ed., pp. 1122, 1123 and title page and verso.
*Journal of Medicinal Chemistry*, 16(11), (1973), pp. 1260–1267; Clarke et al.

*Primary Examiner*—Joseph P. Brust
*Attorney, Agent, or Firm*—James F. Haley; David K. Barr; Eric R. Hubbard

[57] ABSTRACT

A process is disclosed for the preparation of a compound of formula (I):

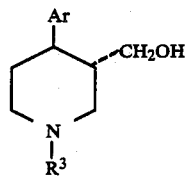

(I)

wherein Ar is aryl or substituted aryl and $R^3$ is hydrogen, alkyl or aralkyl, which process comprises reducing a compound of formula (II):

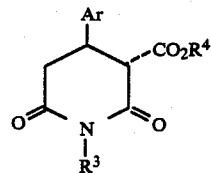

(II)

wherein Ar and $R^3$ are as defined with respect to formula (I) and $R^4$ is alkyl. Compounds of formula (I) are useful as chemical intermediates.

8 Claims, No Drawings

PROCESS FOR PREPARING ARYL-PIPERIDINE CARBINOLS AND NOVEL INTERMEDIATES USED IN THE PROCESS

This invention relates to a novel chemical process for preparing aryl-piperidine carbinols and to novel intermediates used in that process.

British patent No. 1422263 and U.S. Pat. No. 4007196 disclose compounds of formula A

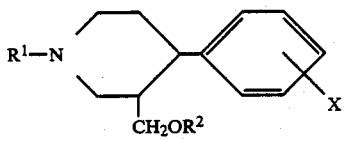

in which $R^1$ represents hydrogen, trifluoro ($C_{1-4}$) alkyl, alkyl or alkynyl, $R^2$ represents an alkyl or alkynyl group having 1-4 carbon atoms, or a phenyl group optionally substituted by $C_{1-4}$ alkyl, alkylthio, alkoxy, halogen, nitro, acylamino, methylsulfonyl or methylenedioxy, or represents tetrahydronaphthyl, and X represents hydrogen, alkyl having 1-4 carbon atoms, alkoxy, trifluoroalkyl, hydroxy, halogen, methylthio, or aralkyloxy.

The compounds of formula A are disclosed as having pharmacological properties that make them useful as anti-depressants. One compound that has proved especially valuable is paroxetine [$R^1$=H, $R^2$=5-(1,3-benzdioxylyl), X=4-F] which is in the (−)-trans configuration.

In the above-mentioned patents, the compounds of formula A are prepared using an intermediate of formula B

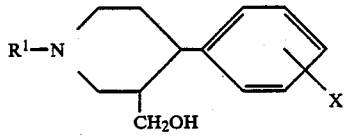

in which $R^1$ and X are as defined above.

The piperidine carbinols of formula B are prepared by reduction of an ester of formula C

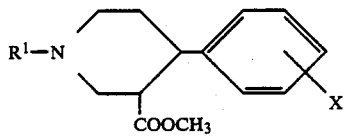

with a complex metal hydride reducing agent.

The compound of formula C is obtained by reacting arecoline (when $R^1$=methyl) or arecoline homologues with phenyl (or substituted phenyl) magnesium bromide.

This procedure has the disadvantage that arecoline is a powerful irritant and that the ester of formula C is obtained as a mixture of cis and trans configuration compounds.

We have now discovered a new process for preparation of piperidine carbinols which advantageously avoids the use of arecoline and selectively produces the trans-isomer in a good overall yield.

Accordingly, the present invention provides a process for preparing a compound of formula I

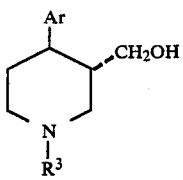

in which Ar represents an aryl or substituted aryl group and $R^3$ represents hydrogen, an alkyl or aralkyl group, by reduction of a compound of formula II

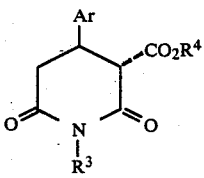

in which Ar and $R^3$ are as defined for formula (I), and $R^4$ is an alkyl group.

In formulae I and II, Ar may be

where X is as defined for formula A. Preferably X is fluorine or hydrogen, $R^3$ is hydrogen, methyl or benzyl, and $R^4$ is ethyl.

The reduction may be carried out conventionally using a metal hydride, for example using lithium aluminium hydride or aluminium hydride in an inert solvent such as tetrahydrofuran or in a tetrahydrofuran/toluene mixture.

The compounds of formula I are obtained in the trans configuration but as a mixture of enantiomers. The compounds may be resolved into their enantiomeric forms by conventional methods, such as by use of an optically active acid, for example (+)-2'-nitrotartranilic acid or (−)-di-p-toluoyltartaric acid.

The compounds of formula I may be used as intermediates in the preparation of compounds of formula A making use of the procedures set out in British Patent No. 1422263 or U.S. Pat. No. 4,007,196.

For example, to prepare paroxetine, the compound of formula I in which

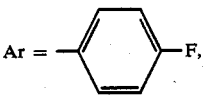

and preferably $R^3$=Me to protect the nitrogen atom, in the (−)-trans-configuration, is reacted with thionyl chloride or benzenesulphonyl chloride and then with sodium 3,4-methylenedioxyphenoxide. Subsequently the N-methyl group is replaced by reaction with phenyl chloroformate followed by de-acylation with KOH to obtain $R^3$=H.

The present invention also provides certain intermediates of formula II as novel compounds. Preferred substituents are as exemplified for formula I.

The compounds of formula II may be prepared by reaction of alkyl amido-malonates of formula III where $R^3$ and $R^4$ are as defined previously:

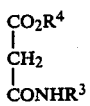
                                                            III with appropriate cinnamic acid esters, such as alkyl and aryl esters, for example, a compound of Formula IV:

                                                            (IV)

where AR is as defined previously and $OR^5$ is a leaving group.

The reaction may be performed as a condensation in a base/solvent system, for example sodium hydride/dimethyl sulphoxide; potassium tert. butoxide in ethanol or tetrahydrofuran; or sodium methoxide or ethoxide in ethyl acetate.

Advantageously the compound of formula II is prepared as a 'single pot' reaction forming the cinnamate in situ from the appropriate benzaldehyde. For example appropiate alkyl amidomalonate is added to a mixture of the benzaldehyde and sodium methoxide in ethyl acetate.

Compounds of formula II in which $R^3$=alkyl or aralkyl may also be prepared by conventional alkylation of compounds of formula II in which $R^3$=H. For example, ester-imides of formula II in which $R^3$=H may be reacted with alkyl or aralkyl halides in the presence of mild bases such as potassium carbonate.

The above described processes for producing the intermediates of formula II also form part of this invention.

As used herein, the terms alkyl, aryl, aralkyl, alkoxy and aralkyloxy include, but are not limited to, groups in which the alkyl moiety, if present, is straight or branched and contains from 1 to 6 carbon atoms, more especially from 1 to 4 carbon atoms, and the aryl moiety, if present, is phenyl.

The following Examples illustrate the preparation of novel intermediates of this invention (Examples 1 to 4) and the novel process of this invention (Examples 5 to 9). Temperatures are in °C.

EXAMPLE 1

(±)-trans-3-Ethoxycarbonyl-4-(4'-fluorophenyl) piperidin-2,6-dione (E1)

Potassium t-butoxide (1.01 g) was added to a solution of ethyl amidomalonate (1.38 g) in tetrahydrofuran (38 ml) maintained at 33°. After cooling to 25°, ethyl 4-fluorocinnamate (1.50 g) was added and the mixture stirred overnight at room temperature. Brine was added, the mixture extracted with ethyl acetate (3×60 ml) and the organic solution dried and evaporated to give the crude product. This was chromatographed on silica gel, using dry ether as eluent, to give the title compound (0.92 g, 43%), m.p. 97°–99°.

$^1$H-n.m.r. (CDCl$_3$) δ=1.07 (t, J=8 Hz, 3H) 2.67–2.90 (m, 2H) 3.50–3.84 (m, 2H) 4.00 (q, J=8 Hz, 2H) 6.70–7.27 (m, 4H) 8.90 (br.s, 1H)

EXAMPLE 2

(±)-trans-3-Ethoxycarbonyl-4-(4'-fluorophenyl)-N-methyl piperidin-2,6-dione (E2)

(a) Sodium hydride (80%, 2.6 g) was added slowly to a stirred solution of ethyl N-methylamidomalonate (11.9 g) in dimethyl sulphoxide (50 ml) under nitrogen. After hydrogen evolution had ceased and the dark solution had cooled to room temperature, ethyl 4-fluorocinnamate (15.3 g) was added in one portion along with further dimethyl sulphoxide (10 ml) and the whole stirred at room temperature for 19 hours. After extraction with petroleum ether (3×16 ml), the mixture was stirred and neutralised by the addition of glacial acetic acid (4.9 ml) followed by the addition of ethyl acetate (75 ml) and water (35 ml). The organic solution was separated, washed with brine (30 ml), sodium bicarbonate solution (22 ml) and brine and finally dried over anhydrous sodium sulphate. Evaporation gave an off-white crystalline solid (22.7 g), which was triturated with isopropyl ether before filtering and drying to give the title compound as a white crystalline solid (20.0 g, 86%), m.p. 91°–96°.

$^1$H-n.m.r. (CDCl$_3$) δ=1.10 (t, J=8 Hz, 3H), 2.75–3.00 (m, 2H), 3.18 (s, 3H), 3.50–3.90 (m, 2H), 4.10 (q, J=8 Hz, 2H), 6.80–7.30 (m, 4H).

(b) A solution of compound E1 (±)-trans-3-ethoxycarbonyl-4(4'-fluorophenyl)piperidin-2,6-dione (1.0 g) in anhydrous dimethylformamide was stirred and cooled to about 0° and methyl iodide (0.67 g) and anhydrous potassium carbonate (0.51 g) added. The mixture was stirred at 0°–2° for 7.5 hours, after which it was diluted with water and extracted with ethyl acetate (100 ml). The extract was washed with water, brine and dried over anhydrous sodium sulphate. Evaporation gave the title compound as a pale yellow oil, ca. 90% pure by n.m.r. spectroscopy.

EXAMPLE 3

(±)-trans-3-Ethoxycarbonyl-4-(4'-fluorophenyl)-piperidin-2,6-dione (E3)

A solution of ethyl amidomalonate (17.5 gms, 1.0 eq at 70%) in ethyl acetate (50 ml) was added to a solution of ethyl cinnamate (21.6 gms, 0.1 m at 90%) in ethyl acetate (200 mls) containing sodium methoxide (7.6 gms) over 0.5 hr at 20° C. The slurry was stirred for 8 hours at 20° C. and 72 hours at 5° C. The slurry was then added to a mixture of water (200 ml) and acetic acid (2.5 eq).

After separation of the rich ethyl acetate the solvent was evaporated under reduced pressure and product was isolated via crystallisation from propan-2-ol by adding heptane.

Yield=5.2 gms

Product was a mixture of 20% methyl, 80% ethyl esters.

Structure confirmed by NMR and HPLC comparison with the N-methyl equivalent. (E2)

EXAMPLE 4

(±)-trans-3-Ethoxycarbonyl-4-(4'-fluorophenyl)-N-methylpiperidin-2,6-dione (E4)

A solution of p-fluorobenzaldehyde (100 g) in ethyl acetate (100 ml) was added slowly to a mixture of sodium methoxide (105 g) in ethyl acetate (900 ml), maintaining the temperature at 10°–20° C. and stirring for a further 30 minutes at 15°–25° C. Then a solution of desiccated ethyl N-methylamidomalonate (139 g) in ethyl acetate (200 ml) was added over 1 hour whilst maintaining the temperature at 15°–25° C. and stirring for a further 1–2 hours. The resulting mixture was added to a solution of acetic acid (120 g) in water (475 ml) and stirred for 15 minutes. The lower aqueous layer was then separated and discarded. The rich solvent was washed with saturated brine (250 ml). The solvent was removed by vacuum distillation and replaced with propan-2-ol then cooled with stirring to obtain the crystalline title compound. Water (600 ml) was added over 30 minutes and the mixture stirred for 1–2 hours at 15°–25° C. The product was filtered and washed with water then isopropyl ether before drying.

Yield=80–90%

EXAMPLE 5

(±)-trans-4-(4'-Fluorophenyl)-3-hydroxymethyl-N-methylpiperidine (E5)

Compound E2 (±)-trans-3-ethoxycarbonyl-4-(4'-fluorophenyl)-N-methylpiperidin-2,6-dione (18.0 g) in tetrahydrofuran (80 ml) was added slowly to a solution of lithium aluminium hydride (6.0 g) in tetrahydrofuran (40 ml) under nitrogen, keeping the temperature below 40°. When addition was complete, the reaction mixture was stirred at room temperature overnight, then warmed to 50° for about 7 hours and finally stirred overnight at room temperature.

Decomposition was effected by the careful addition of water (30 ml) followed by 10% aqueous sodium hydroxide solution (6.0 ml). The hydrolysed mixture was stirred for 1½ hours before filtering off the precipitated salts which were washed with ethyl acetate (50 ml). The filtrate was dried over anhydrous sodium sulphate and evaporated down to give a solid product which was triturated with ether, filtered and dried, to give the title compound (9.0 g, 65%), m.p. 122°–126°.

$^1$H-n.m.r (DMSO-d$_6$) δ=1.56°–1.92 (m, 5H), 2.15°–2.29 (m, 4H), 2.77–2.85 (d, 1H), 2.88–2.99 (m, 1H), 3.02–3.14 (m, 2H), 3.38 (s, 1H), 7.06–7.29 (m, 4H).

Resolution

The title compound E5 (8.6 g) and (+)-2'-nitrotartranilic acid (10.4 g) were dissolved in warm acetone (70 ml) and water (1.9 ml) added. After cooling and allowing to stand at 5° for 2 days, the crystalline salt was filtered off, washed with acetone and dried in vacuo (7.7 g, 39%).

The salt (7.6 g) was suspended in water and a slight excess of dilute hydrochloric acid added to precipitate the tartranilic acid which was filtered off and washed with water. The filtrate was basified with sodium carbonate solution and extracted with ethyl acetate (total 60 ml) and the extracts washed with sodium carbonate solution, water and dried over anhydrous sodium sulphate. Evaporation gave (−)-trans-4-(4'-fluorophenyl)-3-hydroxymethyl-N-methylpiperidine as a crystalline solid which was triturated with ether/petroleum ether (b.p. 60°–80°), filtered and dried (3.1 g, 95% recovery), m.p. 102°–103°, [α]$_D^{26}$ (c=5 in acetone) −37°.

EXAMPLE 6

(±)-trans-4-(4'-Fluorophenyl)-3-hydroxymethylpiperidine

Compound E1 (±)-trans-3-ethoxycarbonyl-4(4'-fluorophenyl)piperidin-2,6-dione (2.0 g) was reduced with lithium aluminium hydride (0.58 g) in refluxing tetrahydrofuran (50 ml) for 4 hours. Work up as described in Example 5 gave the title compound as a solid (0.28 g, 22%).

EXAMPLE 7

(±)-trans-4-(4'fluorophenyl)-3-hydroxymethyl-N-methyl piperidine. (E7)

Compound E4 (34 g) in toluene (150 ml) was added slowly to a slurry of lithium aluminium hydride (10 g) in a tetrahydrofuran (50 ml)/toluene (150 ml) mixture, maintaining the temperature at 0°–5° C. under nitrogen. (Commercially available solutions of lithium aluminium hydride in tetrahydrofuran/toluene have also been used successfully). The mixture was stirred for a further 1–5 hours and then allowed to warm up to 15°–25° C. overnight. The excess lithium aluminium hydride was destroyed by the carefully controlled addition of water (10 ml), dilute 15% sodium hydroxide (10 mls) and water (30 ml). The solids were then removed by filtration and reslurried in toluene (100 ml). The combined rich toluene layers were concentrated to a low volume (75 ml) and poured into petroleum ether [100°–120°] (25 ml). After stirring for 8–24 hours the product was isolated by filtration, washed with petroleum ether (10 ml) and dried.

Yield=65–75%

EXAMPLE 8

(−)-trans-4-(4'Fluorophenyl)-3-hydroxymethyl-N-methyl piperidine

Compound E7 (5 g) was dissolved in acetone (50 ml) and added to a solution of (−)-di-p-toluoyltartaric acid (11.25 g) in acetone (50 ml) at 15°–25° C. The mixture was stirred for 1 hour at 15°–25° C., then a further hour at 0°–10° C. The crystalline salt was filtered off, washed with acetone and dried.

Yield=40–45%

The salt (6 g) was suspended in water and methylene dichloride (MDC). The (−)-trans-4-(4'-fluorophenyl)-3-hydroxymethyl-N-methylpiperidine was extracted into the MDC using sodium hydroxide. Evaporation of the rich MDC gave an oil which was redissolved in toluene. The toluene was removed by evaporation to give an oil. The addition of heptane and trituration gave a crystalline solid which was filtered off and dried.

Yield=85–89%. [α]$_D^{26}$=−35°(c=1% in methanol).

EXAMPLE 9

(±)-trans-4-(4'-Fluorophenyl)-3-hydroxymethyl-N-methyl piperidine (E9)

Lithium aluminium hydride (3.24 g; 0.084 mol) was added with stirring to dry tetrahydrofuran (200 ml) at 0° C. under an atmosphere of nitrogen. Concentrated sulphuric acid (2.16 ml) was then added dropwise and the mixture was stirred at 0° C. for 1 hour to give a solution of aluminium hydride. The imide (E2, 10.0 g; 0.034 mol) was added as a solution in dry tetrahydrofuran (199 ml) and the mixture stirred at 0°–5° C. for 4–5 hours, then at room temperature overnight. Sodium hydroxide (16.2

We claim:

1. A process for the preparation of a compound of formula (I):

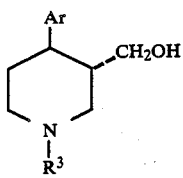

wherein Ar is a group:

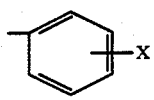

in which X is hydrogen, alkyl having 1–4 carbon atoms, $C_{1-6}$ alkoxy, trifluoro $C_{1-6}$ alkyl, hydroxy, halogen, methylthio, or phenyl $C_{1-6}$ alkoxy and $R^3$ is hydrogen, $C_{1-6}$ alkyl or phenyl $C_{1-6}$ alkyl, which process comprises reducing a compound of formula (II):

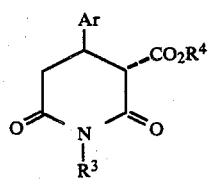

wherein Ar and $R^3$ are as defined with respect to formula (I) and $R^4$ is $C_{1-6}$ alkyl.

2. A process according to claim 1, wherein the reduction is carried out with a metal hydride reducing agent.

3. (±)-trans-3-Ethoxycarbonyl-4-(4'-fluorophenyl)-piperidin-2,6-dione, (±)-trans-3-ethoxycarbonyl-4-(4'-fluorophenyl)-N-methyl piperidin-2,6-dione, or (±)-trans-3-methoxycarbonyl-4-(4'-fluorophenyl)-piperidin-2,6-dione.

4. A process for the preparation of a compound of formula (II):

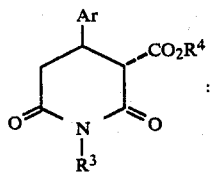

wherein Ar, $R^3$ and $R^4$ are as defined in claim 1, which process comprises (a) reacting a compound of formula (III):

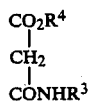

wherein $R^3$ and $R^4$ are as defined with respect to formula (II), with a compound of formula (IV):

wherein Ar is as defined with respect to formula (II) and $OR^5$ is a leaving group, and/or (b) converting a compound of formula (II) wherein $R^3$ is hydrogen to a compound of formula (II) wherein $R^3$ is $C_{1-6}$ alkyl or phenyl $C_{1-6}$ alkyl.

5. A process according to claim 4, wherein a compound of formula (III) as defined in claim 4 is condensed with a compound of formula (IV) as defined in claim 6 in a base/solvent system.

6. A process according to claim 4, wherein a compound of formula (II) wherein $R^3$ is hydrogen is converted to a compound of formula (II) wherein $R^3$ is $C_{1-6}$ alkyl or phenyl $C_{1-6}$ alkyl by reaction with an $C_{1-6}$ alkyl or phenyl $C_{1-6}$ alkyl halide in the presence of a base.

7. A process according to claim 4, wherein a compound of formula (IV) as defined in claim 4 is formed in situ by the base catalysed condensation of a compound of formula ArCHO with an ester of acetic acid.

8. A process for the preparation of a compound of formula (I):

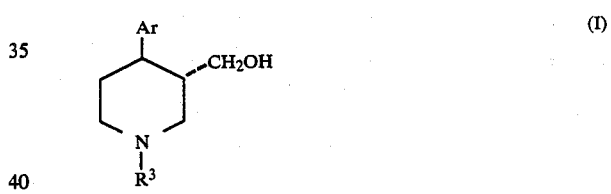

wherein Ar is a group:

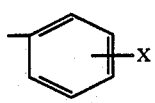

in which X is hydrogen, alkyl having 1–4 carbon atoms, $C_{1-6}$ alkoxy, trifluoro $C_{1-6}$ alkyl, hydroxy, halogen, methylthio, or phenyl $C_{1-6}$ alkoxy and $R^3$ is hydrogen, $C_{1-6}$ alkyl or phenyl $C_{1-6}$ alkyl, which process comprises reducing a compound of formula (II):

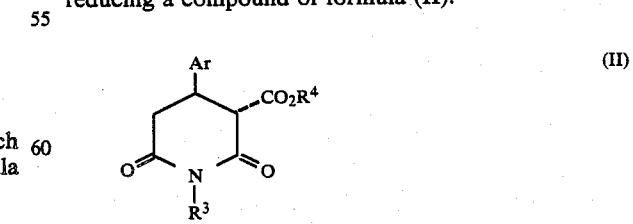

wherein Ar and $R^3$ are as defined with respect to formula (I) and $R^4$ is $C_{1-6}$ alkyl, which is prepared by a process comprising (a) reacting a compound of formula (III):

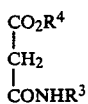
where $R^3$ and $R^4$ are defined with respect to formula (II), with a compound of formula (IV):
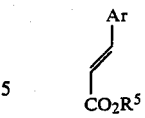
wherein Ar is as defined with respect to formula (II) and $OR^5$ is a leaving group, and/or (b) converting a compound of formula (II) wherein $R^3$ is hydrogen to a compound of formula (II) wherein $R^3$ is $C_{1-6}$ alkyl or phenyl $C_{1-6}$ alkyl.
* * * * *

UNITED STATES PATENT AND TRADEMARK OFFICE
CERTIFICATE OF CORRECTION

PATENT NO. : 4,902,801

DATED : February 20, 1990

INVENTOR(S) : Faruk et al.

It is certified that error appears in the above-identified patent and that said Letters Patent is hereby corrected as shown below:

Column 3, line 19, "AR" should be -- Ar --

Column 3, line 29, "appropiate" should be -- appropriate --

Column 5, line 45, "$\delta$ =1.56°" should be -- $\delta$=1.56 --

Column 5, line 46, "2.15°" should be -- 2.15 --

Column 5, line 68, "C=5" should be -- C=5% --

In the claims:

Claim 5, line 19, "of formula (IV) as defined in claim 6" should be -- of formula (IV) as defined in claim 4. --

Signed and Sealed this

Twenty-fourth Day of September, 1991

Attest:

HARRY F. MANBECK, JR.

*Attesting Officer*  *Commissioner of Patents and Trademarks*